US012594553B2

(12) United States Patent
Adler et al.

(10) Patent No.: US 12,594,553 B2
(45) Date of Patent: Apr. 7, 2026

(54) ELECTRONIC TEST RESULT DETERMINATION AND CONFIRMATION

(71) Applicants: Purdue Research Foundation, West Lafayette, IN (US); RTX BBN Technologies, Inc., Cambridge, MA (US)

(72) Inventors: Aaron Adler, Towson, MD (US); Bryan Bartley, Arlington, MA (US); Mike Gavin, Princeton, NJ (US); Jordan Seville, Delran, NJ (US); Darby McChesney, Lawrenceville, NJ (US); Frank M. LaDuca, Warrensburg, NY (US); Jiangshan Wang, West Lafayette, IN (US); Andres Dextre, West Lafayette, IN (US); Mohit Verma, West Lafayette, IN (US)

(73) Assignees: RTX BBN TECHNOLOGIES, INC., Cambridge, MA (US); PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 17/576,977

(22) Filed: Jan. 16, 2022

(65) Prior Publication Data

US 2022/0252518 A1     Aug. 11, 2022

Related U.S. Application Data

(60) Provisional application No. 63/148,527, filed on Feb. 11, 2021, provisional application No. 63/138,316, (Continued)

(51) Int. Cl.
*G01N 1/44* (2006.01)
*B01L 3/00* (2006.01)
(Continued)

(52) U.S. Cl.
CPC ............... *B01L 3/5023* (2013.01); *B01L 7/00* (2013.01); *C12Q 1/6806* (2013.01);
(Continued)

(58) Field of Classification Search
CPC ........ G01N 1/44; G01N 21/78; G01N 33/526; B01L 3/5023; B01L 7/00; G01J 3/524; G01J 2003/467; G01K 7/02; G01K 7/22
See application file for complete search history.

(56) References Cited

U.S. PATENT DOCUMENTS

| 5,955,377 A | 9/1999 | Maul et al. |
| 6,240,791 B1 | 6/2001 | Kenney |
(Continued)

FOREIGN PATENT DOCUMENTS

| AU | 621236 B2 | 3/1992 |
| AU | 2019213482 A1 | 8/2020 |
(Continued)

OTHER PUBLICATIONS

Wong, Y-P., et al. "Loop-mediated isothermal amplification (LAMP): a versatile technique for detection of micro-organisms." Journal of applied microbiology 124.3 (2018): 626-643. (Year: 2018).*
(Continued)

*Primary Examiner* — Dominic J Bologna
(74) *Attorney, Agent, or Firm* — CANTOR COLBURN LLP

(57) ABSTRACT

A technology is described for a system for identifying a colorimetric test result from a pathogen test performed on a solid phase substrate. The system can comprise a sensor configured to detect a spectrum of color wavelengths. The system can comprise one or more processors. The one or more processors can be configured to: receive color wavelength data; determine a wavelength threshold for providing a pathogen positive test result; identify whether the color (Continued)

wavelength data meets or exceeds the wavelength threshold for providing a pathogen positive test result; and generate a result indicator indicating either a pathogen positive or pathogen negative test result.

16 Claims, 7 Drawing Sheets

Related U.S. Application Data filed on Jan. 15, 2021, provisional application No. 63/138,323, filed on Jan. 15, 2021, provisional application No. 63/138,320, filed on Jan. 15, 2021, provisional application No. 63/138,337, filed on Jan. 15, 2021, provisional application No. 63/138,321, filed on Jan. 15, 2021, provisional application No. 63/138,318, filed on Jan. 15, 2021, provisional application No. 63/138,312, filed on Jan. 15, 2021, provisional application No. 63/138,314, filed on Jan. 15, 2021, provisional application No. 63/138,310, filed on Jan. 15, 2021, provisional application No. 63/138,341, filed on Jan. 15, 2021.

(51) Int. Cl.

| | |
|---|---|
| *B01L 7/00* | (2006.01) |
| *C12Q 1/6806* | (2018.01) |
| *C12Q 1/6844* | (2018.01) |
| *C12Q 1/6848* | (2018.01) |
| *C12Q 1/6888* | (2018.01) |
| *C12Q 1/70* | (2006.01) |
| *G01J 3/46* | (2006.01) |
| *G01J 3/52* | (2006.01) |
| *G01K 7/02* | (2021.01) |
| *G01K 7/22* | (2006.01) |
| *G01N 21/78* | (2006.01) |
| *G01N 33/52* | (2006.01) |

(52) U.S. Cl.

CPC ......... *C12Q 1/6844* (2013.01); *C12Q 1/6848* (2013.01); *C12Q 1/6888* (2013.01); *C12Q 1/70* (2013.01); *C12Q 1/701* (2013.01); *G01J 3/524* (2013.01); *G01K 7/02* (2013.01); *G01K 7/22* (2013.01); *G01N 1/44* (2013.01); *G01N 21/78* (2013.01); *G01N 33/526* (2013.01); *B01L 2200/04* (2013.01); *B01L 2200/0689* (2013.01); *B01L 2200/10* (2013.01); *B01L 2200/16* (2013.01); *B01L 2300/0681* (2013.01); *B01L 2300/069* (2013.01); *B01L 2300/0809* (2013.01); *B01L 2300/0825* (2013.01); *B01L 2300/0832* (2013.01); *B32B 2250/04* (2013.01); *C12Q 2600/112* (2013.01); *G01J 2003/467* (2013.01)

(56) References Cited

U.S. PATENT DOCUMENTS

| | | | |
|---|---|---|---|
| 7,682,565 B2 | 3/2010 | Linton et al. | |
| 10,619,189 B2 | 4/2020 | Sitton et al. | |
| 10,968,493 B1 | 4/2021 | Tanner et al. | |
| 2002/0150501 A1 | 10/2002 | Robertson et al. | |
| 2006/0000296 A1 | 1/2006 | Salter | |
| 2007/0046941 A1* | 3/2007 | Mestha | G01J 3/50 |
| | | | 356/402 |
| 2008/0194426 A1 | 8/2008 | Goodman et al. | |
| 2008/0268495 A1 | 10/2008 | Skold et al. | |
| 2010/0291588 A1 | 11/2010 | Mcdevitt et al. | |
| 2010/0331725 A1 | 12/2010 | Libby et al. | |
| 2011/0150705 A1 | 6/2011 | Doyle et al. | |
| 2011/0165595 A1 | 7/2011 | Catanzaro et al. | |
| 2011/0171754 A1 | 7/2011 | Redmond et al. | |
| 2012/0142070 A1 | 6/2012 | Battrell et al. | |
| 2013/0130257 A1 | 5/2013 | Hillebrand et al. | |
| 2013/0132006 A1 | 5/2013 | Gwynn et al. | |
| 2014/0154789 A1 | 6/2014 | Polwart et al. | |
| 2014/0170661 A1 | 6/2014 | Lamura et al. | |
| 2015/0346105 A1 | 12/2015 | Gutsell et al. | |
| 2015/0353919 A1 | 12/2015 | Mielke et al. | |
| 2016/0008809 A1 | 1/2016 | Li et al. | |
| 2016/0139156 A1* | 5/2016 | Lakdawala | G01N 21/8483 |
| | | | 436/87 |
| 2016/0231251 A1 | 8/2016 | Ou et al. | |
| 2016/0310948 A1 | 10/2016 | Nowakowski et al. | |
| 2016/0319354 A1 | 11/2016 | Tocigl et al. | |
| 2017/0248622 A1 | 8/2017 | Khattak et al. | |
| 2018/0021777 A1 | 1/2018 | Giri et al. | |
| 2018/0141041 A1 | 5/2018 | Paek | |
| 2018/0299385 A1* | 10/2018 | Honda | G01N 33/54366 |
| 2018/0313743 A1 | 11/2018 | Dixon et al. | |
| 2019/0083975 A1 | 3/2019 | Mitra et al. | |
| 2019/0092536 A1 | 3/2019 | Freedman et al. | |
| 2019/0218604 A1 | 7/2019 | Liang et al. | |
| 2019/0226985 A1 | 7/2019 | Roberts et al. | |
| 2019/0369094 A1* | 12/2019 | Ishikawa | G16H 50/80 |
| 2020/0063197 A1* | 2/2020 | Meldrum | G01N 21/78 |
| 2020/0126226 A1* | 4/2020 | Adiri | G06T 7/0012 |
| 2020/0181720 A1* | 6/2020 | Abudayyeh | C12Q 1/68 |
| 2020/0309702 A1* | 10/2020 | Barron | G01N 21/6486 |
| 2021/0275663 A1 | 9/2021 | Jiao et al. | |
| 2022/0160581 A1 | 5/2022 | Rigby | |
| 2022/0203365 A1* | 6/2022 | Abraham | G16B 25/20 |
| 2022/0226817 A1 | 7/2022 | Horvath et al. | |
| 2022/0228205 A1 | 7/2022 | Seville et al. | |
| 2022/0228226 A1 | 7/2022 | Seville et al. | |
| 2022/0228956 A1 | 7/2022 | Horvath et al. | |
| 2022/0235408 A1 | 7/2022 | Adler et al. | |
| 2022/0280081 A1* | 9/2022 | Andeshmand | B01L 3/502761 |
| 2022/0290261 A1 | 9/2022 | Davidson et al. | |
| 2022/0291246 A1 | 9/2022 | Joris et al. | |
| 2022/0340984 A1 | 10/2022 | Seville et al. | |
| 2022/0380858 A1 | 12/2022 | Gavin et al. | |
| 2022/0403460 A1 | 12/2022 | Horvath et al. | |
| 2023/0014132 A1 | 1/2023 | Seville et al. | |
| 2024/0376492 A1 | 11/2024 | Christen | |

FOREIGN PATENT DOCUMENTS

| | | |
|---|---|---|
| AU | 2022207504 A1 | 6/2023 |
| CA | 3203454 A1 | 7/2022 |
| CN | 107419027 A | 12/2017 |
| CN | 108384870 A | 8/2018 |
| CN | 111330002 A | 6/2020 |
| CN | 111378784 A | 7/2020 |
| CN | 111500778 A | 8/2020 |
| CN | 111518947 A | 8/2020 |
| CN | 112111607 A | 12/2020 |
| CN | 112342318 A | 2/2021 |
| CN | 112739833 A | 4/2021 |
| EP | 4277997 A1 | 11/2023 |
| EP | 4278010 A1 | 11/2023 |
| JP | 2013519884 A | 5/2013 |
| JP | 2014198029 A | 10/2014 |
| JP | 2015062406 A | 4/2015 |
| JP | 2016534357 A | 11/2016 |
| JP | 2018515100 A | 6/2018 |
| JP | 2024504297 A | 1/2024 |
| WO | 2008101732 A1 | 8/2008 |
| WO | WO 2013/067272 A1 | 5/2013 |
| WO | WO 2014/152656 A1 | 9/2014 |
| WO | 2015033229 A2 | 3/2015 |
| WO | WO 2015/103293 A2 | 7/2015 |
| WO | WO 2016/183012 A1 | 11/2016 |
| WO | WO 2017/160836 A1 | 9/2017 |
| WO | WO 2018/170340 A1 | 9/2018 |
| WO | 2019073049 A1 | 4/2019 |
| WO | WO 2019/109092 A1 | 6/2019 |
| WO | 2019149963 A1 | 8/2019 |

(56) References Cited

FOREIGN PATENT DOCUMENTS

| WO | 2020084637 A1 | 4/2020 |
| WO | WO 2020/251460 A1 | 12/2020 |
| WO | WO 2020/257356 A2 | 12/2020 |
| WO | 2021183921 A1 | 9/2021 |
| WO | WO 2021/216728 A1 | 10/2021 |
| WO | 2022155546 A1 | 7/2022 |
| WO | 2022155547 A1 | 7/2022 |
| WO | 2022155548 A1 | 7/2022 |

OTHER PUBLICATIONS

Babu, Uma S., et al. "A loop-mediated isothermal amplification (LAMP) assay for the consensus detection of human pathogenic Campylobacter species." Journal of microbiological methods 176 (2020): 106009. (Year: 2020).*

Dou, Maowei et al.; "A Versatile PDMS/Paper Hybrid Microfluidic Platform for Sensitive Infectious Disease Diagnosis"; Anal. Chem. 86, pp. 7978-7986 (2014).

Dou, Maowei et al.; "A Versatile PDMS/Paper Hybrid Microfluidic Platform for Sensitive Infectious Disease Diagnosis"; Anal. Chem. 86, pp. 7978-7986; Supplemental S1-S7 (2014).

Nery, E.W. et al.; "Sensing approaches on paper-based devices: a review," Anal. Bioanal. Chem.; 405; pp. 7573-7595 (2013).

Bhadra, Sanchita et al.; High-surety isothermal amplification an detection of SARS-CoV-2, including with crude enzymes bioRxiv; Jul. 7, 2020; SP055912874; DOI: 10.1101/2020.04.13.039941.

Carrio, Adrian et al.; "Automated Lo-Cost Smartphone-Based Lateral Flow Saliva Test Reader for Drugs-of-Abuse Detection" Sensors; vol. 15, No. 12; Nov. 24, 2015; pp. 29569-29593; XP055257628; DOI: 10.3390/s151129569.

Davidson, Josiah Levi et al.; "A paper-based colorimetric molecular test for SARS-CoV-2 in saliva" Biosensors and Bioelectronics: X; vol. 9; Dec. 9, 2021; p. 100076; XP055911157; https://doi.org/10.1016/j.biosx.2021.100076.

Ganguli, A et al.; "Hands-free smartphone-based diagnostics for simultaneous detection of Zika, Chikungunya, and Dengue at point-of-care" Biomedical Microdevices; vol. 19, No. 4; Aug. 22, 2017; pp. 1-13; XP036372395; ISSN: 1387-2176; DOI: 10.1007/S10544-017-0209-9.

Hardinge, Patrick et al.; "Reduced False Positives and Improved Reporting of Loop-Mediated Isothermal Amplification using Quenched Fluorescent Primers" Scientific Reports; vol. 9, No. 1; Dec. 1, 2019; XP055912878; DOI: 10.1038/s41598-019-43817-z.

Howson, Emma et al.; "Preliminary optimization of a simplified sample preparation method to permit direct detection of SARS-CoV-2 within saliva samples using reverse-transcription loop-medicated isothermal amplification (RT-LAMP)" Journal of Virological Methods, Elsevier BV, NL; vol. 289; Dec. 20, 2020; XP086476416; ISSN: 0166-0934; DOI: 10.1016/j.jviromet.2020.114048.

Huang, Wei E.; "RT LAMP for rapid diagnosis of coronavirus SARS-CoV-2" Microbial Biotechnology; vol. 13, No. 4; Apr. 25, 2020; pp. 950-961; XP055733462; ISSN: 1751-7915; DOI: 10.1111/1751-7915.13586.

Kellner, Max J. et al.; A rapid, highly sensitive and open-access SARS-CoV-2 detection assay for laboratory and home testing; bioRxiv; Jun. 23, 2020; XP055911082; DOI: 10.1101/2020.06.23.166397.

LaBarre, Paul et al.; "Instrument-free nucleic acid amplification assays for global health settings" Sensing Technologies for Gloval Health, Military Medicine, Disaster Response, and Environmental Monitoring; and Biometric Technology for Human Identification VIII; SPIE; vol. 8029, No. 1; May 13, 2011; pp. 1-15; XP060014496.

Lalli, Matthew et al.; "Rapid and extraction-free detection of SARS-CoV-2 from saliva with colorimetric LAMP" medRxiv; Aug. 6, 2020; pp. 1-34; XP055791998; DOI: 10.1101/2020.05.07.20093542; www.ncbi.nlm.nih.gov/pmc/articles/PMC7273276/pdf/nihpp-2020.05.07.20093542.pdf.

Momen-Heravi, Fatemeh; "Impact of Biofluid Viscosity on Size and Sedimentation Efficiency of the Isolated Microvesicles" Frontiers in Physiology; vol. 3; Jan. 1, 2012; XP055189135; ISSN: 1664-042X; DOI: 10.3389/fphys.2012.00162.

Park, Gun-Soo et al.; "Development of Reverse Transcription Loop-Mediated Isothermal Amplification Assays Targeting Severe Acute Respiratory Syndrome Coronavirus 2 (SARS-CoV-2)" The Journal of Molecular Diagnostics; vol. 22, No. 6; Jun. 1, 2020; pp. 729-735; XP055796358; https://doi.org/10.1016/j.jmoldx.2020.03.006.

Qian, Jason et al.; "An enhanced isothermal amplification assay for viral detection" Nature Communications; vol. 11, No. 1; Nov. 2020; XP055870470; DOI: 10.1038/s41467-020-19258-y; http://www.nature.com/articles/s41467-020-19258-y.

Rabe, Brian, et al.; SARS-CoV-2 detection using isothermal amplification and a rapid, inexpensive protocol for sample inactivation and purification' Proceedings of the National Academy of Sciences; vol. 117, No. 39; Sep. 8, 2020; pp. 24450-24458; XP055910088; ISSN: 0027-8424; DOI: 10.1073/pnas.2011221117.

Safavieh, Mohammadali et al.; "Emerging Loop-Mediated Isothermal Amplification-Based Microchip and Microdevice Technologies for Nucleic Acid Detection" ACS Biometerials Science and Engineering; vol. 2, No. 3; Mar. 14, 2016; pp. 278-294; XP055872000; ISSN: 2373-9878.

Schermer, Bernard et al.; "Rapid SARS-CoV-2 Testing in Primary Material Based on a Novel Multiplex RT-LAMP Assay" PLOS One; vol. 15, No. 11; Nov. 2, 2020; pp. 1-13 XP055824117; https://doi.org/10.1371/journal.pone.0238612.

Stedtfeld, Robert D. et al.; "Static self-directed sample dispensing into a series of reaction wells on a microfluidic card for parallel genetic detection of microbial pathogens" Biomedical Microdevices, Springer US, New York; vol. 17, No. 5; Aug. 11, 2015; pp. 1-12; XP035552426; ISSN: 1387-2176; DOI: 10.1007/S10544-015-9994-1.

Svendsen, Winnie E.; "Lab-on-a-Chip Devices and Micro-Total Analysis Systems" In: Department of Micro- and Nan0technology Technical University of Denmark Kgs. Lyngby Denmark; Oct. 9, 2015; XP055714359; ISBN: 978-3-319-08687-3; pp. 112-113.

Tanner, Nathan et al.; "Visual detection of isothermal nucleic acid amplification using pH-sensitive dyes" Biotechniques; vol. 58, No. 2; Feb. 1, 2015; pp. 59-68; SP055245831; DOI: 10.2144/000114253.

Thapa, Jeewan et al.; "Direct detection of Mycobacterium tuberculosis in clinical samples by a dry methyl green loop-mediated isothermal amplification (LAMP) method" Tuberculosis, Elsevier, SG; vol. 117; May 21, 2019; pp. 1-6; XP085754043; ISSN: 1472-9792; DOI: 10.1016/J.TUBE/2019.05.004.

Thompson, Dorian et al.; "Mini review: Recent progress in RT-LAMP enabled Covid-19 detection" Sensors and Actuators reports; Aug. 15, 2020; XP055911165; www.ncbi.nlm.nih.gov/pmc/articles/PMC7428436/pdf/main/pdf.

Yang, Qing et al.; "Saliva TwoStep for rapid detection of symptomatic SARS-CoV-2 carriers" ELIFE; vol. 10; Mar. 29, 2021; XP055875382; DOI: 10.7554/eLife.65113.

Yin, Kun et al.; "Synergistically enhanced colorimetric molecular detection using smart cup: a case for instrument-free HPV-associated cancer screening" Theranositics; vol. 9, No. 9; Jan. 1, 2019; pp. 2637-2645; XP055911179; ISSN: 1838-7460; DOI: 10.7150/thno.32224.

Zhang, Yinhua et al.; "Enhancing colorimetric loop-mediated isothermal amplification speed and sensitivity with guanidine chloride" Biotechniques; vol. 69, No. 3; Sep. 1, 2020; pp. 178-185; XP055888013; ISSN: 0736-6205; DOI: 10.2144/btn-2020-0078.

Baliga et al.; "Salivary pH: A diagnostic biomarker"; Journal of Indian Society of Periodontology, vol. 17, Issue No. 4; pp. 461-465 (2013) DOI:10.4103/0972-124X. 118317.

Helton et al.; Conditioning saliva for use in microfluidic biosensor; Lab Chip, 2008, 8, 1847-1851.

Robinson et al.; Use of Throat Swab or Saliva Specimens for Detection of Respiratory Viruses in Children; Clinical Infectious Diseases; 2008:46; 4 pages.

Non Final Office Action for application U.S. Appl. No. 17/576,970, dated Feb. 15, 2024, 77 pages.

(56)          References Cited

OTHER PUBLICATIONS

AU Examination Report, Application No. 2022207504, date of mailing Nov. 22, 2024, 4 pages.
AU Examination Report, Application No. 2022208714, date of mailing Nov. 25, 2024, 4 pages.
AU Examination Report; Application No. 2022207503, date of mailing Nov. 22, 2024, 4 pages.
Brown, T. et al.; "Direct detection of SARS-CoV-2 RNA using high-contrast pH-sensitive dyes"; Journal of Biomolecular Techniques, vol. 32, Issue No. 3; pp. 121-133; DOI:10.7171/jbt.21-3203-007 (2021).
CA Office Action for Application No. 3,203,298, mailed May 30, 2024, 5 pages.
CA Office Action for Application No. 3,203,453, mailed Jul. 31, 2024, 6 pages.
CA Office Action for Application No. 3,203,454, mailed Jul. 29, 2024, 4 pages.
EP Office Action for Application No. 22703180.4, mailed Nov. 14, 2023, 4 pages.
JP Office Action for Patent Application No. 2023-542512, mailed Jul. 30, 2024, 11 pages.
JP Office Action for Patent Application No. 2023-542674, mailed Jul. 2, 2024, 20 pages.
JP Office Action for Patent Application No. 2023-542850, mailed Aug. 20, 2024, 9 pages.
Kaarj, et al. "Simpler, Faster, and sensitive Zika Virus Assay Using Smartphone Detection of Loop-mediated Isothermal Amplification on Paper Microfluidic Chips", Scientific Reports, (2018) 8: 12438; pp. 1-11.
International Search Report and the Written Opinion of the International Searching Authority, or the Declaration; PCT/US2022/012634; Apr. 20, 2022, 13 pages.
International Search Report and the Written Opinion of the International Searching Authority, or the Declaration; PCT/US2022/012635; Apr. 22, 2022, 11 pages.
International Search Report and the Written Opinion of the International Searching Authority, or the Declaration; PCT/US2022/012636; Apr. 25, 2022, 12 pages.
International Search Report and the Written Opinion of the International Searching Authority, or the Declaration; PCT/US2022/012637; May 16, 2022, 11 pages.
International Search Report and the Written Opinion of the International Searching Authority, or the Declaration; PCT/US2022/012639; Apr. 26, 2022, 13 pages.
International Search Report and the Written Opinion of the International Searching Authority, or the Declaration; PCT/US2022/012640; Apr. 26, 2022, 13 pages.
International Search Report and the Written Opinion of the International Searching Authority, or the Declaration; PCT/US2022/012641; Apr. 20, 2022, 18 pages.
International Search Report and the Written Opinion of the International Searching Authority, or the Declaration; PCT/US2022/012642; Jul. 13, 2022, 18 pages.
International Search Report and the Written Opinion of the International Searching Authority, or the Declaration; PCT/US2022/016183; Jul. 25, 2022, 22 pages.
Rodriguez, N. et al.; "Paper-Based RNA Extraction in Situ Isothermal Amplification and Lateral Flow Detection for Low-Cost Rapid Diagnosis of Influenza A (H1N1) from Clinical Specimens"; Anal Chem 87; pp. 7872-7879 (2015).
Bst DNA polymerase—NEB pdf—Downloaded from Internet on Dec. 1, 2024. (Year: 2024), 5 pages.
CA Office Action for Application No. 3,203,298, mailed Feb. 24, 2025, 4 pages.
EP Office Action for Application No. 22703177.0, mailed Feb. 20, 2025, 8 pages.
European Office Action, Application No. 22703179.6, mailed Mar. 13, 2025, 7 pages.
European Office Action, Application No. 22704038.3, mailed Mar. 14, 2025, 8 pages.

European Office Action, Application No. 22707530.6, mailed Mar. 17, 2025, 5 pages.
Farshidfar, et al., "The Potential Role of Smartphone-Based Microfluidic Systems for Rapid Detection of COVID-19 Using Saliva Specimen", Aug. 1, 2020, Molecular Diagnosis & Therapy; vol. 24, No. 4; 2020; pp. 371-373; 3 pages.
Hyun et al., "Salivary Exosome and Cell-Free DNA for Cancer Detection", Jul. 4, 2018, Micromachines 2018, vol. 9, No. 7; MDPI; 13 pages.
International Office Action; JP Application No. 2023542512, mailed Jan. 21, 2025; 5 pages; with machine translation.
Japan Office Action, Application No. 2023-542850, mailed Mar. 4, 2025, with English Translation, 7 pages, machine translation.
Japanese Office Action, Application No. 2023542674, mailed Mar. 18, 2025, with machine translation, 13 pages.
Miocevic, et al., "Quantitative Lateral Flow Assays for Salivary Biomarker Assessment: A Review", Frontiers in Public Health; vol. 5 Article 133; Jun. 2017;13 pages.
Notification of Transmittal of the International Preliminary Report on Patentability; PCT/US2022/012635; Jul. 4, 2023, 7 pages.
Notification of Transmittal of the International Preliminary Report on Patentability; PCT/US2022/012636; Jul. 4, 2023, 8 pages.
Notification of Transmittal of the International Preliminary Report on Patentability; PCT/US2022/012637; Jul. 4, 2023,8 pages.
Oasis ("Pure-SALTM: Oral Specimen Collection System" Oasis diagnostics, 2016, Vancouver WA) (Year: 2016), 10 pages.
Promega ("TE Buffer", available at https://www.promega.com/products/biochemicals-and-labware/biochemcial-buffers-and-reagents/te-buffer_-1x_-molecular-biology-grade/?catNUM=V6231, accessed on Nov. 26, 2024) (Year: 2024), 5 pages.
Reuter, et al., "Loop-mediated amplification as promising on-site detection approach for Legionelle pneumophila and Legionelle spp", Dec. 12, 2019, Applied Microbiology and Biotechnology, col. 104 No. 1, (2020), pp. 405-415, 11 pages.
Schroff, "100% Solids: A compelling solution to the challenge of medical adhesive coating", SAE Media Group, 2015, 8 pages.
Seok et al., "Lab-on-paper for all-in-one molecular diagnostics (LAMDA) of zika, dengue, and chikungunya virus from human serum", Biosensors and Bioelectronics 165 (2020), 8 pages.
Seok,, "A Paper-Based Device for Performing Loop-Mediated Isothermal Amplification with Real-Time Simultaneous Detection of Multiple DNA Targets", Theranostics vol. 7, ZIssue 8, 2017, p. 2220-2230; 11 pages.
Short, et al. "Effect of Interfacing on colorimetric reactions for deoxyribonucelic acid", Anal. Biochem. 1986, p. 251-268.
WarmStart® RTx Reverse Transciptase—NEB pdf—downloaded from Internet on Dec. 1, 2024. (Year: 2024), 3 pages.
Yager, et al., "Microfluidic diagnostic technologies for global public health", Nature; vol. 442, Jul. 2006, pp. 412-418; 8 pages.
Adhesives Research. Point of Care Innovative Solutions [online] Adhesives Research; Oct. 2020 [retrieved Jun. 27, 2025] Available from: https://www.adhesivesresearch.com/china/wp-content/uploads/2010/10/Point-of-Care-Innovative-Solutions.pdf (Year: 2020).
Ahn et al., "Rapid and simple colorimetric detection of multiple influenza viruses infecting humans using a reverse transcriptional loop-mediated isothermal amplification (RT-LAMP) diagnostic platform" BMC Infectious Diseases, vol. 19 (2019) p. 676.
Byers et al. "Versatile printed microheaters to enable low-power thermal control in paper diagnostics" Analyst 145.1 (2020) pp. 184-196.
CalculatorSoup L. Rectangular prism calculator (cuboid) [online] [retrieved Jun. 27, 2025] Available from: https://www.calculatorsoup.com/calculators/geometry-solids/rectangularprism.php (Year 2023).
Carter et al. "Lyophilized visually readable loop-mediated isothermal reverse transcriptase nucleic acid amplification test for detection Ebola Zaire RNA" Journal of virological methods 244 (Jun. 2017) pp. 32-38.
Grade 1 qualitative filter paper, standard, 30mm circle, 100/PK [online] [retrieved Jun. 27, 2025] Available from: https://www.tischscientific.com/whatman/filter-papers-cellulose-filters-qualitative-filter-papers-1001-329 (Year: 2025).

(56) References Cited

OTHER PUBLICATIONS

Lin et al., "Influence of water evaporation/absorption on the stability of glycerol-water marbles" RSC Advances, vol. 9 (2019) p. 34465.

Marshall Scientific "Biorad CFX96 touch real-time PCR system" [online] 2025 [retrieved Sep. 10, 2025] Retrieved from the internet: https://www.marshallscientific.com/Biorad-CFX96-Touch-Real-Time-PCR-System-p/bio-cfx96t.htm.

Naik et al., "Nucleic Acid amplification on paper substrates" Paper Microfluidics (2019) pp. 115-146.

Office Action issued in Australian Patent Application No. 2022207504; Date of Mailing Aug. 27, 2025 (4 pages).

Surface area of a cylinder—formula, TSA and CSA [online] [retrieved Jun. 27, 2025] Available from: https://www.cuemath.com/measurement/surface-area-of-cylinder (Year: 2025).

Tian et al. "Development of a fluorescent-intercalating-dye-based reverse transcription loop-mediated isothermal amplification assay for rapid detection of seasonal Japanese B encephalitis outbreaks in pigs" Archives of virology 157.8 (2012) pp. 1481-1488 Abstract Only.

Trantidou et al., "Hydrophilic surface modification of PDMS for droplet microfluids using a simple, quick, and robust method via PVA deposition" Microsyst Nanoeng (Apr. 2017) (9 pages).

Whatman Laboratory Filtration Product Guide [online] GE Healthcare Bio-Sciences Corp [retrieved Jun. 26, 2025] Retrieved from: https://static.fishersci.eu/content/dam/fishersci/en_EU/suppliers/Whatman/Whatman_Lab_Filtration_Product_Guide2.pdf (Year: 2018).

Montrasio "Development of a software application for loop-mediated isothermal amplification (LAMP) primer design" (Year: 2016) 137 pages.

Office Action issued in Japanese Patent Application No. 2023-542512; Date of Mailing Jul. 8, 2025 (17 pages).

Safavieh et al., "A simple cassette as point-of-care diagnostic device for naked-eye colorimetric bacteria detection" Analyst 139.2 (2014) pp. 482-487.

Search Report issued in Taiwan Application No. 111101755; Date of Mailing Jun. 19, 2025 (10 pages).

Search Report issued in Taiwan Application No. 111101759; Date of Mailing Jun. 19, 2025 (9 pages).

Zhou et al. "A mismatch-tolerant reverse transcription loop-mediated isothermal amplification method and its application on simultaneous detection of all four serotype of dengue viruses" Front Microbiol (May 2019) 13 pages.

Office Action issued in Taiwan Patent Application No. 111101754; Date of Mailing Sep. 19, 2025 (11 pages).

Office Action issued in Taiwan Patent Application No. 111101756; Date of Mailing Sep. 18, 2025 (11 pages).

Rodriguez et al. "based RNA extraction, in situ isothermal amplification, and lateral flow detection for low-cost, rapid diagnosis of influenza A (H1N1) from clinical specimens" Analytical chemistry 87.15 (Aug. 2015) pp. 7872-7879.

Safavieh et al. "Emerging loop-mediated isothermal amplification-based microchip and microdevice technologies for nucleic acid detection" ACS biomaterials science & engineering 2.3 (Mar. 2016) pp. 278-294.

Yin et al. "Synergistically enhanced colorimetric molecular detection using smart cup: a case for instrument-free HPV-associated cancer screening" Theranostics 9.9 (Apr. 2019) 9 pages.

Kaarj et al., "Simpler, faster, and sensitive Zika virus assay using smartphone detection of loop-mediated isothermal amplification on paper microfluidic chips" Scientific reports 8.1 (Aug. 2018) 11 pages.

Office Action issued in Taiwanese Application No. 111101752; Date of Mailing Oct. 13, 2025 (12 pages).

Office Action issued in Korean Patent Application No. 10-2023-7025878; Date of Mailing Nov. 4, 2025 (17 pages).

Thi, V. L. D. et al.; "A colorimetric RT-LAMP assay and LAMP-sequencing for detecting SARS-CoV-2 RNA in clinical samples"; Science Translational Medicine, DOI: 10.1126/scitranslmed.abc7075, 2020, vol. 12, Issue 556.

Wan et al. "Development of a test kit for visual loop-mediated isothermal amplification of Salmonella in spiked ready-to-eat fruits and vegetables" Journal of microbiological methods 169 (Feb. 2020) 10 pages.

Wei et al. "Field-deployable, rapid diagnostic testing of saliva for SARS-CoV-2" Scientific reports 11.1 (Mar. 2021) 10 pages.

Office Action issued in Korean Patent Application No. 10-2023-7025868; Date of Mailing Nov. 21, 2025 (191 pages).

* cited by examiner

400 receive color wavelength data          410 determine a wavelength threshold for providing a pathogen positive test result          420 identify whether the color wavelength data meets or exceeds the wavelength threshold for providing a pathogen positive test result          430 generate a result indicator indicating either a pathogen positive or pathogen negative test result          440

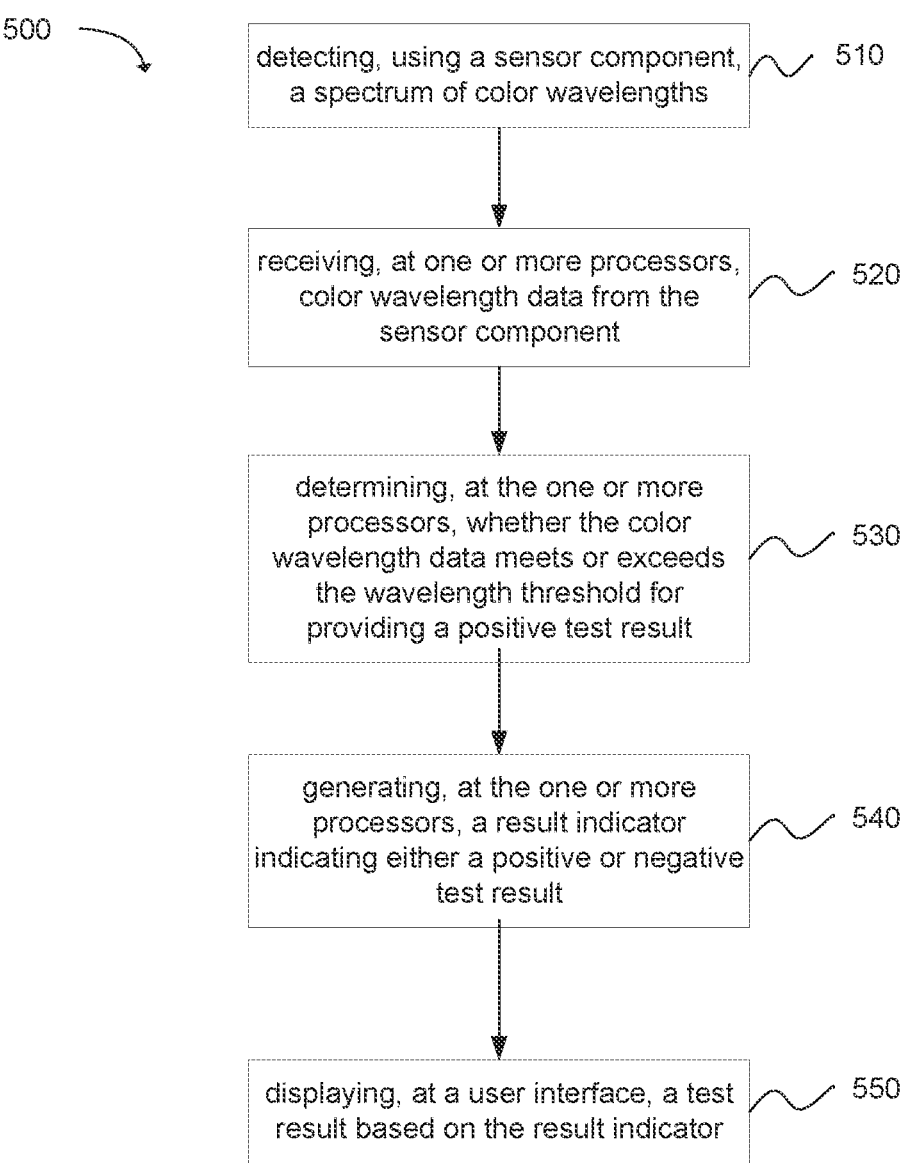

500 detecting, using a sensor component, a spectrum of color wavelengths — 510 receiving, at one or more processors, color wavelength data from the sensor component — 520 determining, at the one or more processors, whether the color wavelength data meets or exceeds the wavelength threshold for providing a positive test result — 530 generating, at the one or more processors, a result indicator indicating either a positive or negative test result — 540 displaying, at a user interface, a test result based on the result indicator — 550

FIG. 5

600 receiving color wavelength data from a sensor component                    610 determining whether the color wavelength data exceeds a wavelength threshold for providing a positive test result for a pathogen test          620 generating a result indicator indicating either a positive or negative test result          630

ELECTRONIC TEST RESULT DETERMINATION AND CONFIRMATION

This application claims the benefit of U.S. Provisional Patent Application Ser. No. 63/138,310 filed Jan. 15, 2021, U.S. Provisional Patent Application Ser. No. 63/138,312 filed Jan. 15, 2021, U.S. Provisional Patent Application Ser. No. 63/138,314 filed Jan. 15, 2021, U.S. Provisional Patent Application Ser. No. 63/138,316 filed Jan. 15, 2021, United States Provisional Patent Application Ser. No. 63/138,318 filed Jan. 15, 2021, U.S. Provisional Patent Application Ser. No. 63/138,320 filed Jan. 15, 2021, U.S. Provisional Patent Application Ser. No. 63/138,321 filed Jan. 15, 2021, U.S. Provisional Patent Application Ser. No. 63/138,323 filed Jan. 15, 2021, U.S. Provisional Patent Application Ser. No. 63/138,337 filed Jan. 15, 2021, U.S. Provisional Patent Application Ser. No. 63/138,341 filed Jan. 15, 2021, U.S. Provisional Patent Application Ser. No. 63/148,527 filed Feb. 11, 2021, the entire contents of each of which are incorporated herein by reference.

BACKGROUND

A rapid diagnostic test (RDT) for infectious diseases typically refers to lateral-flow immunochromatographic tests used to detect infections. In some cases, but not always, an RDT may constitute a point-of-care (POC) test. For example, some molecular diagnostics, e.g., polymerase chain reaction (PCR), may only be available at a central laboratory that has access to top bench equipment for performance at a prohibitive cost. Consequently, many RDTs that may be used at a hospital and subsequently shipped for testing are impracticable in other use cases including large-scale (e.g., a concert, mall, university), medium scale (day care, restaurant, café), retail health, and at the home.

Even when a RDT is available in a POC setting, the use and interpretation of the test can be complicated and confusing to many users. The sensitivity of rapid antigen tests for influenza is low and should not be used to dictate therapeutical decisions. Rapid tests for rotavirus and norovirus are less sensitive than molecular tests. Therefore, rapid diagnostic tests that are applicable at the point of care are in high demand.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 5 depicts a method of identifying a test result of a loop-mediated isothermal amplification (LAMP) reaction on a solid phase reaction medium in accordance with an example embodiment;

Figure 1:
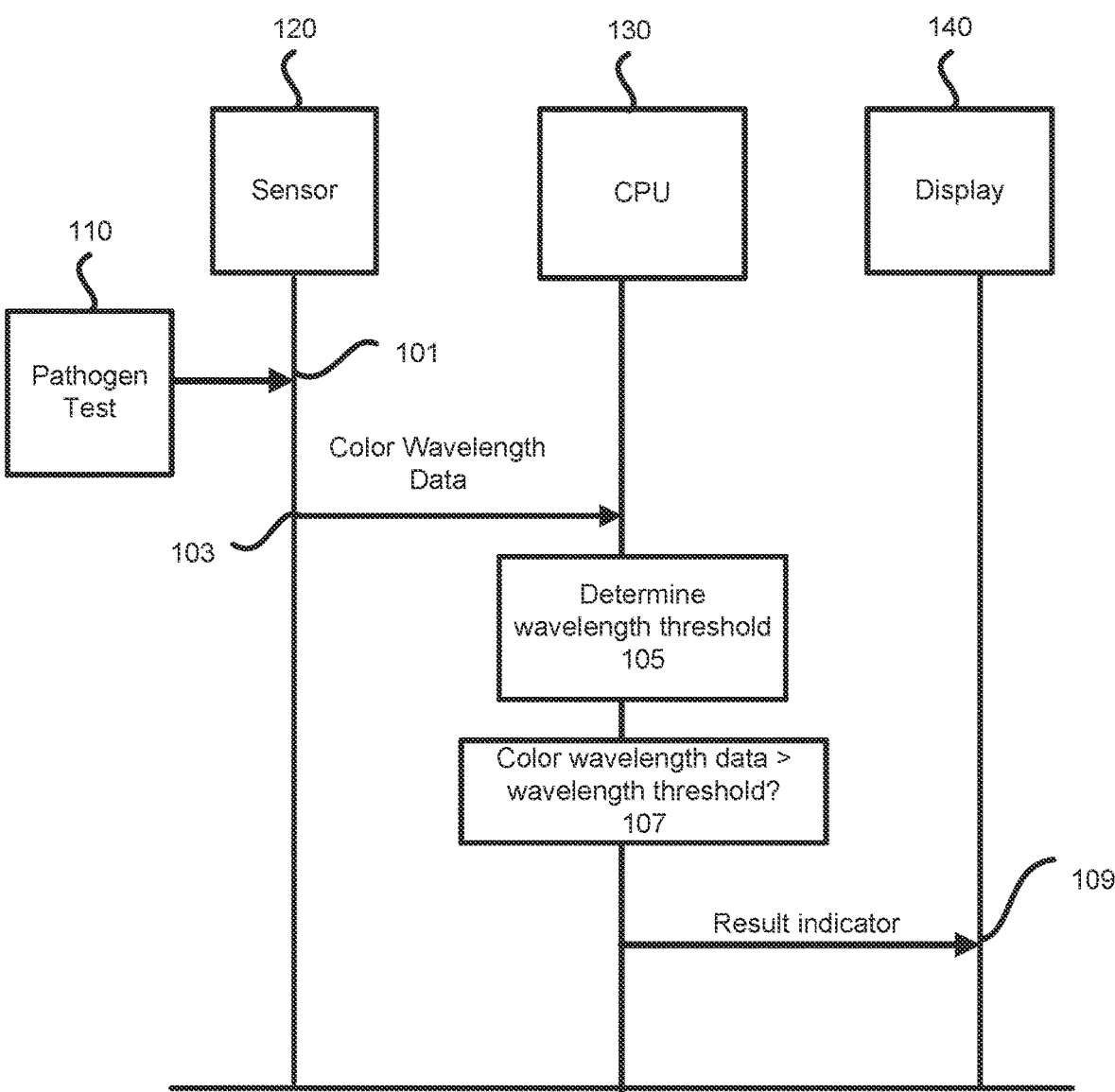
FIG. 1 depicts a flowchart for identifying a colorimetric test result from a pathogen test performed on a solid phase substrate in accordance with an example embodiment.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various invention embodiments. One skilled in the relevant art will recognize, however, that such detailed embodiments do not limit the overall technological concepts articulated herein, but are merely representative thereof.

As used in this written description, the singular forms "a," "an" and "the" include express support for plural referents unless the context clearly dictates otherwise. Thus, for example, reference to "a sensor" includes a plurality of such sensors.

Reference throughout this specification to "an example" means that a particular feature, structure, or characteristic described in connection with the example is included in at least one embodiment of the present invention. Thus, appearances of the phrases "in an example" or "an embodiment" in various places throughout this specification are not necessarily all referring to the same embodiment.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present technology can be referred to herein along with alternatives for the various components thereof. It is understood that such embodiments, examples, and alternatives are not to be construed as de facto equivalents of one another, but are to be considered as separate and autonomous representations under the present disclosure.

Furthermore, the described features, structures, or characteristics can be combined in any suitable manner in one or more embodiments. In the following description, numerous specific details are provided, such as examples of layouts, distances, network examples, etc., to provide a thorough understanding of invention embodiments. One skilled in the relevant art will recognize, however, that the technology can be practiced without one or more of the specific details, or with other methods, components, layouts, etc. In other instances, well-known structures, materials, or operations may not be shown or described in detail to avoid obscuring aspects of the disclosure.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in this written description, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "coupled" and "connected" can be used interchangeably and refer to a relationship between items or structures that are either directly or indirectly connected in an electrical or nonelectrical manner. "Directly coupled" or "directly connected" objects or elements are in physical contact with one another. In this written description, recitation of "coupled" or "connected" provides express support for "directly coupled" or "directly connected" and vice versa. Objects described herein as being "adjacent to" each other may be in physical contact with each other, in close proximity to each other, or in the same general region or area as each other, as appropriate for the context in which the phrase is used.

Occurrences of the phrase "in one embodiment," or "in one aspect," herein do not necessarily all refer to the same embodiment or aspect.

As used herein, comparative terms such as "increased," "decreased," "better," "worse," "higher," "lower,"

"enhanced," "maximized," "minimized," and the like refer to a property of a device, component, or activity that is measurably different from other devices, components, or activities in a surrounding or adjacent area, in a single device or in multiple comparable devices, in a group or class, in multiple groups or classes, or as compared to the known state of the art. For example, a sensor with "increased" sensitivity can refer to a sensor in a sensor array which has a lower level or threshold of detection than one or more other sensors in the array. A number of factors can cause such increased sensitivity, including materials, configurations, architecture, connections, etc.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

Numerical amounts and data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

EXAMPLE EMBODIMENTS

An initial overview of technology embodiments is provided below and then specific technology embodiments are described in further detail later. This initial summary is intended to aid readers in understanding the technology more quickly but is not intended to identify key features or essential features of the technology nor is it intended to limit the scope of the claimed subject matter.

Viral pathogens can spread from pre-symptomatic and asymptomatic individuals. Individuals can remain infectious for up to ten days in moderate cases, and up to two weeks in severe cases. One diagnosis method is by real-time reverse transcription polymerase chain reaction (rRT-PCR) from a nasopharyngeal swab, but results are not usually available for at least a few hours to about a few days. Delays in testing can often led to delays in treatment and delays in mitigating the risk of further spreading the disease.

The utility of a rapid diagnostic test for pathogens is mitigated by the access to the expensive laboratories used to process test results. In many cases, a person afflicted with a disease would not know test results until after: (1) the person has submitted a biological sample at a healthcare facility; (2) the healthcare facility has processed and shipped the biological sample to a laboratory; (3) the laboratory has tested the sample (which can be limited by supplies and personnel); (4) the laboratory has sent the results back to the healthcare facility; (5) the medical personnel at the healthcare facility have analyzed the results; and (6) the medical personnel communicate the test results to the person afflicted with the disease. A rapid diagnostic test that is also a point of care (POC) test (i.e. a short test time with decision-affecting results that can be delivered in the same encounter between a diseased person and healthcare personnel) would provide a further benefit.

When a timely test result can be obtained from a rapid diagnostic test, a POC test can provide an additional enhancement when errors in accuracy or undue uncertainty from the test result are minimized. Some potential sources of testing error include when a test result falsely indicates that a diseased person does not have a disease (a false negative) or falsely indicates that a healthy person does have a disease (a false positive). Additional sources of testing error can include: (i) a clinician error in interpreting the test results, or (ii) a user error in interpreting the test results. These clinician and user errors can be caused by inadequate knowledge, poor critical thinking skills, a lack of competency, issues in data gathering, failing to synthesize information, and the like. In some cases, testing equipment errors can lead to clinician/user errors, and clinician/user errors can also lead to testing equipment errors. As a result, a rapid diagnostic test that can be used in a POC setting while also minimizing testing equipment errors and clinician/user interpretation errors would also be beneficial.

Even when a timely test result can be obtained and the foregoing errors are minimized, the test can provide an uncertain result when the test is inconclusive and an additional test or a different test is used to provide additional information. Therefore, a rapid diagnostic test in a POC setting that minimized testing equipment errors, minimized clinician/user interpretation errors, and minimized uncertain results would be desirable.

In one disclosure embodiment, systems for identifying a colorimetric test result from a pathogen test performed on a solid phase substrate can comprise a sensor configured to detect a spectrum of color wavelengths, and one or more processors. The one or more processors can be configured to receive color wavelength data. The one or more processors can be configured to determine a wavelength threshold for providing a pathogen positive test result. As used herein, a wavelength threshold can be a threshold based on intensity levels at one or more wavelengths. The one or more processors can be configured to identify whether the color wavelength data meets or exceeds the wavelength threshold for providing a pathogen positive test result. The one or more processors can be configured to generate a result indicator indicating either a pathogen positive or pathogen negative test result.

In another disclosure embodiment, methods of identifying a test result of a loop-mediated isothermal amplification (LAMP) reaction on a solid phase reaction medium can comprise detecting, using a sensor component, a spectrum of color wavelengths. The method can further comprise receiving, at one or more processors, color wavelength data from the sensor component. The method can further comprise determining, at the one or more processors, whether the color wavelength data meets or exceeds the wavelength threshold for providing a positive test result. The method can further comprise generating, at the one or more processors, a result indicator indicating either a positive or negative test result. The method can further comprise displaying, at a user interface, a test result based on the result indicator.

In one embodiment, as illustrated with reference to FIG. 1, a system for identifying a colorimetric test result from a pathogen test performed on a solid phase substrate can comprise a sensor 120 configured to detect a spectrum of color wavelengths from a pathogen test 110, as shown in operation 101.

In one aspect, the system can further comprise one or more processors 130 or a CPU 130. In one example, the one or more processors 130 can be configured to receive color wavelength data, as shown in operation 103. In one example, the color wavelength data can include data received by a sensor 120 including one or more of a photoconductive sensor, a photovoltaic sensor, a photodiode sensor, a phototransistor sensor, or combinations thereof a photoresistor, a photodiode array, a charge-coupled device (CCD) camera, a complementary metal-oxide semiconductor (CMOS) camera, the like, or combinations thereof.

In another example, the one or more processors 130 can be configured to determine a wavelength threshold for providing a pathogen positive test result, as shown in operation 105. In another example, the one or more processors 130 can be configured to identify whether the color wavelength data meets or exceeds the wavelength threshold for providing a pathogen positive test result, as shown in operation 107. In yet another example, the one or more processors 130 can be configured to generate a result indicator indicating either a pathogen positive or pathogen negative test result, as shown in operation 109. The one or more processors 130 can be configured to send the result indicator to a display 140, as shown in operation 109.

Figure 2:
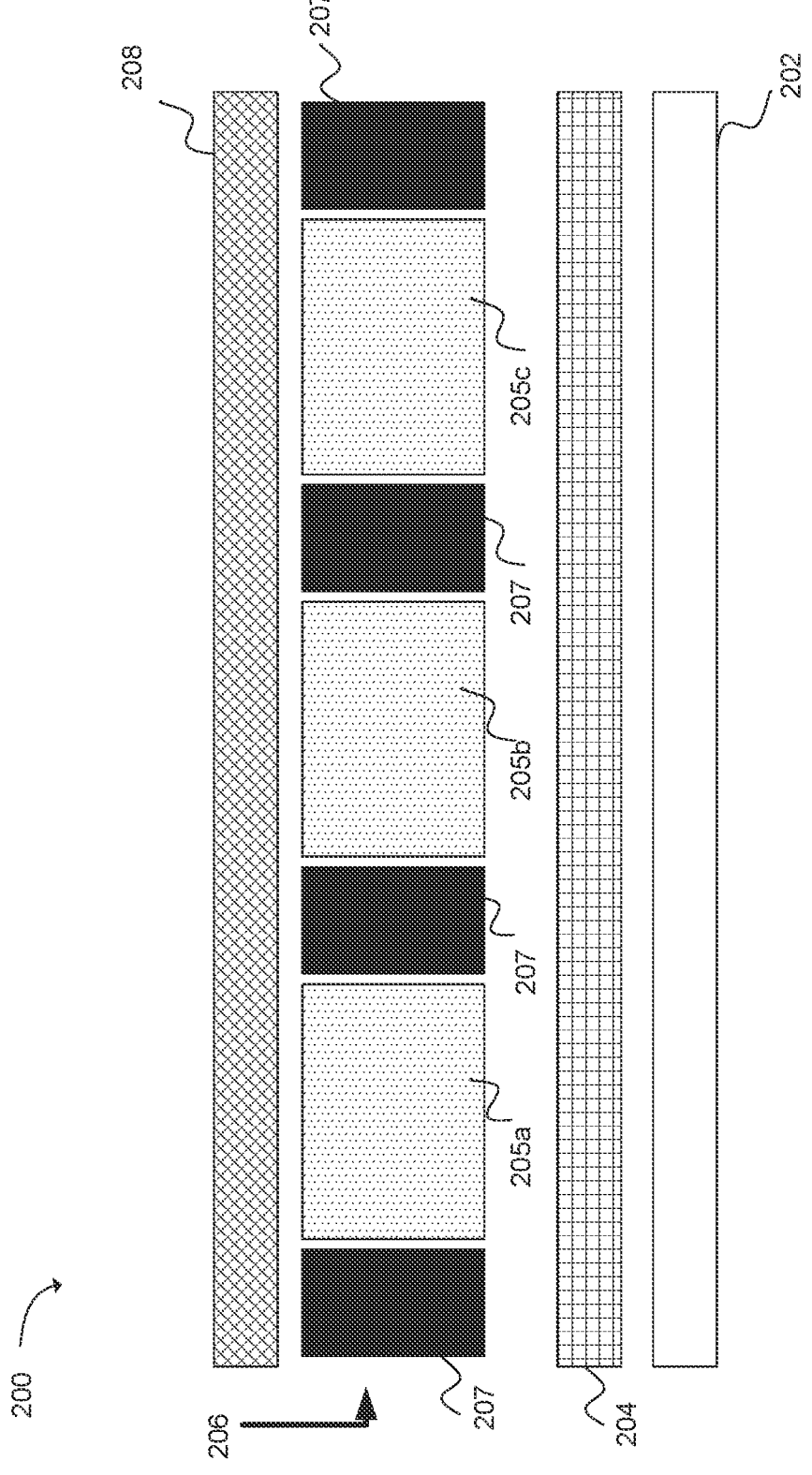
FIG. 2 depicts a pathogen test performed on a solid phase substrate in accordance with an example embodiment.

In another aspect, as illustrated in FIG. 2, a pathogen test system 200 can comprise one or more of a substrate 202, an adhesive layer 204, a reaction layer 206 comprising one or more reaction sections 205a, 205b and 205c, a plurality of spacing layers 207 separating the one or more reaction sections 205a-c, or a spreading layer 208. In one aspect, a sensor can be configured to detect color wavelength data from the one or more reaction sections 205a, 205b and 205c from the reaction layer 206.

Figure 3:
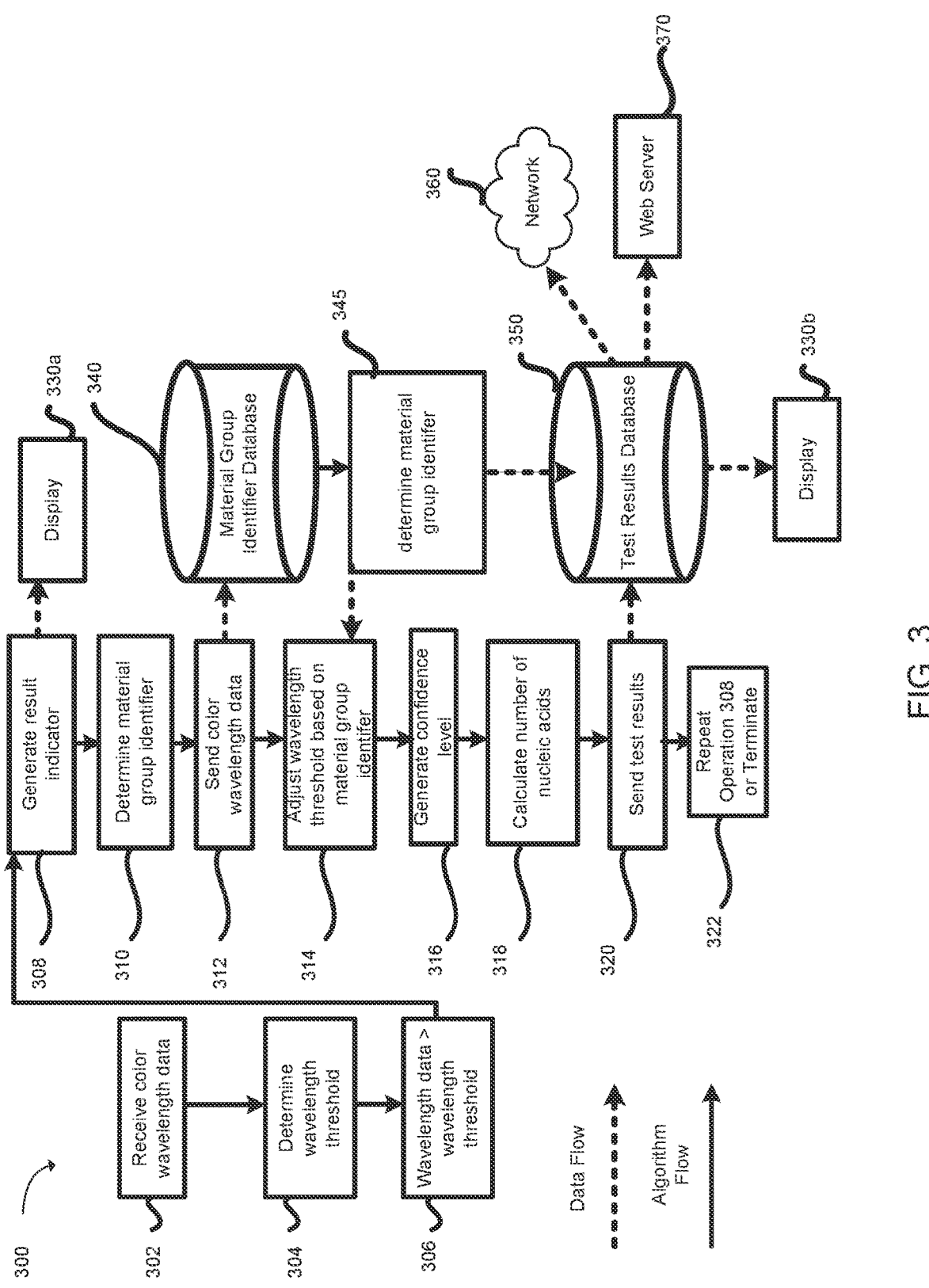
FIG. 3 depicts a flowchart for generating a confidence level in accordance with an example embodiment.

In another aspect, as depicted in the flowchart 300 in FIG. 3, the one or more processors can be configured to receive color wavelength data from one or more sensors, as shown in operation 302. The color wavelength data can be received from discrete sections of a pathogen test (e.g., reaction sections 205a, 205b or 205c), wherein each discrete section can be directed to the same pathogen or different pathogens. The one or more processors can be configured to determine a wavelength threshold, as shown in operation 304. The one or more processors can be configured to determine that the color wavelength data meets or exceeds the color wavelength threshold, as shown in operation 306. The one or more processors can be configured to generate the test result indicator, as shown in operation 308. The one or more processors can be configured to send the test result indicator to a display 330*a*.

A material group identifier can be used to identify the characteristics of reaction layers associated with a manufacturing group. In another aspect, the one or more processors can be configured to determine a material group identifier, as shown in operation 310. The material group identifier in operation 310 can be based on one or more of an average color wavelength of a material group, a median color wavelength of the material group, a variance of the color wavelength of the material group, a manufacturing date and time of the material group, one or more reagent types of the material group, or one or more solid-phase reaction medium types of the material group, the like, or combinations thereof.

The one or more processors can be configured to send the color wavelength data to a material group identifier database 340, as shown in operation 312. The material group identifier database 340 can be configured to determine the material group identifier based on crowd-sourced information, as shown in operation 345. The material group identifier database 340 can send the material group identifier to the one or more processors. The material group identifier database 340 can send the material group identifier to a test results database 350.

The material group identifier database can exchange information from multiple devices. The material group identifier can use the collected information to constantly update the determination of the material group identifier by the material group identifier database when color wavelength data is received from a device (e.g., when operation 345 is performed).

In another aspect, the one or more processors can be configured to adjust the wavelength threshold based on the material group identifier, as shown in operation 314. The one or more processors can be configured to generate a confidence level, as shown in operation 316. The one or more processors can be configured to calculate a number of nucleic acids, as shown in operation 318. The one or more processors can be configured to send the test results to the test results database 350 as shown in operation 320, or repeat operation 308 or terminate, as shown in operation 322.

In one aspect, operation 308 can be repeated when the confidence level is below a selected threshold. For example, when the confidence level is less than about 95%, then operation 308 can be repeated through an iterative process until the confidence level has reached the threshold of 95%. In another aspect, the operation 308 can be repeated until the operation has been repeated a selected number of times. For example, when operation 308 has been repeated about 5 times, then the process can terminate.

In another aspect, the test results can be accessed from the test results database 350 via a display 330*b*, a network 360, or a web server 370.

In some cases, the one or more processors can adjust the wavelength threshold based on the material group identifier without sending or receiving information to the material group identifier database 340. In this case, the material group can be included with the device.

In another aspect, the one or more processors can be configured to adjust the wavelength threshold based on a material group identifier. In one aspect, the material group identifier can be based on one or more of: an average color wavelength of a material group, a median color wavelength of the material group, a variance of the color wavelength of the material group, a manufacturing date and time of the material group, one or more reagent types of the material group, or one or more solid-phase reaction medium types of the material group, the like, or combinations thereof.

In another aspect, the one or more processors can be configured to generate the material group identifier from color wavelength data aggregated from crowd-sourced data. In one aspect, the crowd-sourced data can be associated with a plurality of users associated with the pathogen test. In one aspect, a confidence level of can be calculated from metadata associated with color wavelength data including one or more of a ratio of the number of aggregated test results from a specific material group identifier to the number of total test results from the specific group identifier; a variance of the aggregated test results associated with the specific material group identifier; a date and time when the aggregated test results are received from a user for each material group identifier, the like, or combinations thereof.

In another aspect, the one or more processors can be configured to adjust the wavelength threshold using color wavelength data having a wavelength from about 500 nm to about 565 nm. In one example, the color wavelength data can be adjusted based on a colorimetric range associated with a pH-sensitive dye (e.g., phenol red).

In another aspect, the one or more processors can be configured to calculate a number of nucleic acid copies based on one or more of the color wavelength data, the material group identifier, a color change time, or a rate of color change time. In one example, the number of nucleic acid copies can be calculated using data associated with the material group identifier including, but not limited to, an average color wavelength of a material group, a median color wavelength of the material group, a variance of the color wavelength of the material group, a manufacturing date and time of the material group, one or more reagent types of the material group, or one or more solid-phase reaction medium types of the material group.

In another example, the color change time can be the time between the initialization of a LAMP reaction and a positive test result. In one example, when the color change time for a material group averages about 30 minutes, and the color change time for the pathogen test is about 20 minutes, then the concentration of the pathogen can be higher than the average concentration for the average of the material group. In another example, when the change time for the pathogen test is about 40 minutes, then the concentration of the pathogen can be lower than the average concentration for the average of the material group. The concentration of the pathogen can be calibrated against the material group to provide an approximate number of copies of nucleic acid per volume.

In another aspect, the one or more processors can be configured to generate a confidence level using the color wavelength data and the material group identifier. In one example, a confidence level can be calculated using data associated with the material group identifier including, but not limited to, an average color wavelength of a material group, a median color wavelength of the material group, a variance of the color wavelength of the material group, a manufacturing date and time of the material group, one or more reagent types of the material group, or one or more solid-phase reaction medium types of the material group.

In yet another aspect, the one or more processors can be further configured to receive the color wavelength data for discrete sections (e.g., reaction sections 205a, 205b or 205c) of the pathogen test. In one example, the color wavelength data can be received from a first reaction section of a pathogen test and a second reaction section of a pathogen test, wherein the first reaction section and the second reaction section can be configured to test for the same pathogens or different pathogens.

In yet another aspect, the one or more processors can be further configured to determine the wavelength threshold for providing a pathogen positive test result based on the color wavelength data for discrete sections of the pathogen test. In one example, a first reaction section of the pathogen test can be configured to have a first range of color wavelength data and a second reaction section of the pathogen test can be configured to have a second range of color wavelength data. In another example, a first reaction section of the pathogen test can be configured to the same range of color wavelength data as the second reaction section of the pathogen test.

In yet another aspect, the one or more processors can be further configured to identify whether the color wavelength data meets or exceeds the threshold for providing the pathogen positive test result. In one example, the threshold for the color wavelength data can be the same for each discrete section. When the threshold is the same for the discrete sections, the additional data can provide a positive or negative test result with additional certainty compared to a test result based on color wavelength data from one section.

In another example, the threshold for the color wavelength data can be different for each discrete section (e.g., reaction sections 205a, 205b or 205c). In this example, the threshold for each discrete section can be based on a confidence level. In one example, a first threshold, when met or exceeded, may provide a confidence level of about 95%, while a second threshold, when met or exceeded, may provide a confidence level of about 99%. The confidence level for each section can be based on the quality of color wavelength data obtained. In one example, the quality of color wavelength obtained can differ based on the type of colorimetric indicator used in the pathogen test.

In yet another aspect, the one or more processors can be further configured to generate a confidence level for the pathogen positive test result based on the color wavelength data received from the discrete sections of the pathogen test (e.g., reaction sections 205a, 205b or 205c).

In yet another aspect, the one or more processors can be further configured to: receive the color wavelength data for discrete sections of the pathogen test (e.g., reaction sections 205a, 205b or 205c); determine an additional wavelength threshold for providing a different pathogen positive test result based on the color wavelength data for discrete sections of the pathogen test, and generate an additional result indicator indicating either an additional pathogen positive or additional pathogen negative test result when the discrete sections of the pathogen test are targeted to different pathogens. In one example, a first section of the pathogen test can be targeted to SARS-CoV-2 and the second section of the pathogen test can be targeted to influenza. In one aspect, the confidence level for a positive or negative test result for a first pathogen can be based on the confidence level for a positive or negative test result for a second pathogen. For example, a confidence level of about 90% for a positive test for influenza can negatively affect the confidence level for a positive test result for SARS-CoV-2.

In yet another aspect, the sensor can comprise an RGB sensor configured to generate RGB values or a CMYK sensor configured to generate CMYK values. In one example, the one or more processor can be configured to receive the RGB values from the RGB sensor. The one or more processors can be configured to determine a wavelength threshold for providing a pathogen positive test result based on the RGB values. The one or more processors can be configured to identify whether the color wavelength data meets or exceeds the wavelength threshold for providing a pathogen positive test result based on the RGB values. The one or more processors can be configured to generate a result indicator indicating either a pathogen positive or pathogen negative test result based on the RGB values.

In one example, the one or more processor can be configured to receive the CMYK values from the CMYK sensor. The one or more processors can be configured to determine a wavelength threshold for providing a pathogen positive test result based on the CMYK values. The one or more processors can be configured to identify whether the color wavelength data meets or exceeds the wavelength threshold for providing a pathogen positive test result based on the CMYK values. The one or more processors can be configured to generate a result indicator indicating either a pathogen positive or pathogen negative test result based on the CMYK values.

In another aspect, the sensor can comprise a white light emitter, and a light receiver having a 540 nm filter. In one aspect, the white light emitter can be configured to emit white light towards the pathogen test. In one example, the reflected light intensity from a reaction layer of the pathogen test can be detected using a light receiver having a 540 nm filter. In another example, the reflected light intensity from the reaction layer from the pathogen test can be detected using a light receiver having a filter configured to detect a wavelength in a testing range for the pathogen test.

In yet another aspect, the sensor can comprise one or more of: a photoconductive sensor, a photovoltaic sensor, a photodiode sensor, a phototransistor sensor, or combinations thereof. In another example, the sensor can comprise one or more of a photoresistor, a photodiode array, a charge-coupled device (CCD) camera, a complementary metal-oxide semiconductor (CMOS) camera, the like, or combinations thereof.

In yet another aspect, the system can further comprise a graphical user interface for interacting with a user. The graphical user interface can include a display screen configured to display: (i) an inconclusive test result, (b) the pathogen negative test result, or (c) the pathogen positive test result. In another example, the display screen can be configured to display other aspects of the tests results including one or more of the color wavelength data, the wavelength threshold, the material group identifier, the confidence level, the number of nucleic acids, the pathogens that are negative or positive, the like, or combinations thereof.

In one example, the pathogen can comprise a viral pathogen, a bacterial pathogen, a fungal pathogen, or a protozoa pathogen. In one aspect, the pathogen can comprise a viral pathogen. In one example, the viral pathogen can comprise a dsDNA virus, an ssDNA virus, a dsRNA virus, a positive-strand ssRNA virus, a negative-strand ssRNA virus, an ssRNA-RT virus, or a ds-DNA-RT virus. In one example, each primer sequence can match a sequence from a viral target comprising H1N1, H2N2, H3N2, H1N1pdm09, or SARS-CoV-2.

In another aspect, instead of a pathogen, the specific target nucleotide sequences to be detected can be target nucleotides corresponding to human biomarkers. Any disease that has a target nucleotide corresponding to a human biomarker for a disease can be detected. Various types of diseases can be detected including one or more of: breast cancer, pancreatic cancer, colorectal cancer, ovarian cancer, gastrointestinal cancer, cervix cancer, lung cancer, bladder cancer, many types of carcinomas, salivary gland cancer, kidney cancer, liver cancer, lymphoma, leukemia, melanoma, prostate cancer, thyroid cancer, stomach cancer, the like, or combinations thereof. For example, biomarkers for various types of diseases can be detected by detecting target nucleotides corresponding to one or more of: alpha fetoprotein, CA15-3 and CA27-29, CA19-9, C!-125, calcitonin, calretinin, carcinoembryonic antigen, CD34, CD99MIC 2, CD117, chromogranin, chromosomes 3, 7, 17, and 9p21, cytokeratin, cesmin, epithelial membrane antigen, factor VIII, CD31 FL1, glial fibrillary acidic protein, gross cystic disease fluid protein, hPG80, HMB-45, human chorionic gonadotropin, immunoglobulin, inhibin, keratin, lymphocyte marker, MART-1, Myo D1, muscle-specific actin, neurofilament, neuron-specific enolase, placental alkaline phosphatase, prostate-specific antigen, PTPRC, S100 protein, smooth muscle action, synaptophysin, thymidine kinase, thyroglobulin, thyroid transcription factor-1, tumor M2-PK, vimentin, the like, or combinations thereof.

In another embodiment, a method of identifying a test result of a loop-mediated isothermal amplification (LAMP) reaction on a solid phase reaction medium can comprise detecting, using a sensor component, a spectrum of color wavelengths. In one aspect, the method can comprise receiving, at one or more processors, color wavelength data from the sensor component. In another aspect, the method can comprise determining, at the one or more processors, whether the color wavelength data meets or exceeds the wavelength threshold for providing a positive test result. In another aspect, the method can comprise generating, at the one or more processors, a result indicator indicating either a positive or negative test result. In another aspect, the method can comprise displaying, at a user interface, a test result based on the result indicator.

In another aspect, the method can comprise adjusting, at the one or more processors, the wavelength threshold using RGB values or CMYK values from a material group identifier. In another aspect, the method can comprise receiving, at the one or more processors, RGB values or CMYK values from the spectrum of color wavelengths. In another aspect, the method can comprise generating, at the one or more processors, the result indicator indicating either the positive or negative test result based on the RGB or CMYK values.

In yet another embodiment, at least one machine readable storage medium can have instructions embodied thereon for identifying a test result of a loop-mediated isothermal amplification (LAMP) reaction, wherein the instructions when executed by one or more processors can perform the following: receiving, at the one or more processors, color wavelength data from a sensor component. In another aspect, the instructions when executed can perform: determining, at the one or more processors, whether the color wavelength data exceeds a wavelength threshold for providing a positive test result. In another aspect, the instructions when executed can perform: generating, at the one or more processors, a result indicator indicating either a positive or negative test result. In another aspect, the instructions when executed can perform adjusting the wavelength threshold based on a material group identifier.

In another aspect, the material group identifier can be based on one or more of: an average color wavelength of a material group, a median color wavelength of the material group, a variance of the color wavelength of the material group, a manufacturing date and time of the material group, one or more reagent types of the material group, or one or more solid-phase reaction medium types of the material group. In another aspect, the instructions when executed can perform generating the material group identifier from color wavelength data aggregated from crowd-sourced data. In another aspect, the instructions when executed can perform calculating a number of nucleic acid copies based on the color wavelength data and the material group identifier. In another aspect, the instructions when executed can perform generating a confidence level using the color wavelength data and the material group identifier.

In another aspect, the instructions when executed can perform: generating, at the one or more processors, a result indicator indicating either a positive or negative test result for a plurality of pathogens based on color wavelength data received for discrete sections of the pathogen test.

Figure 4:
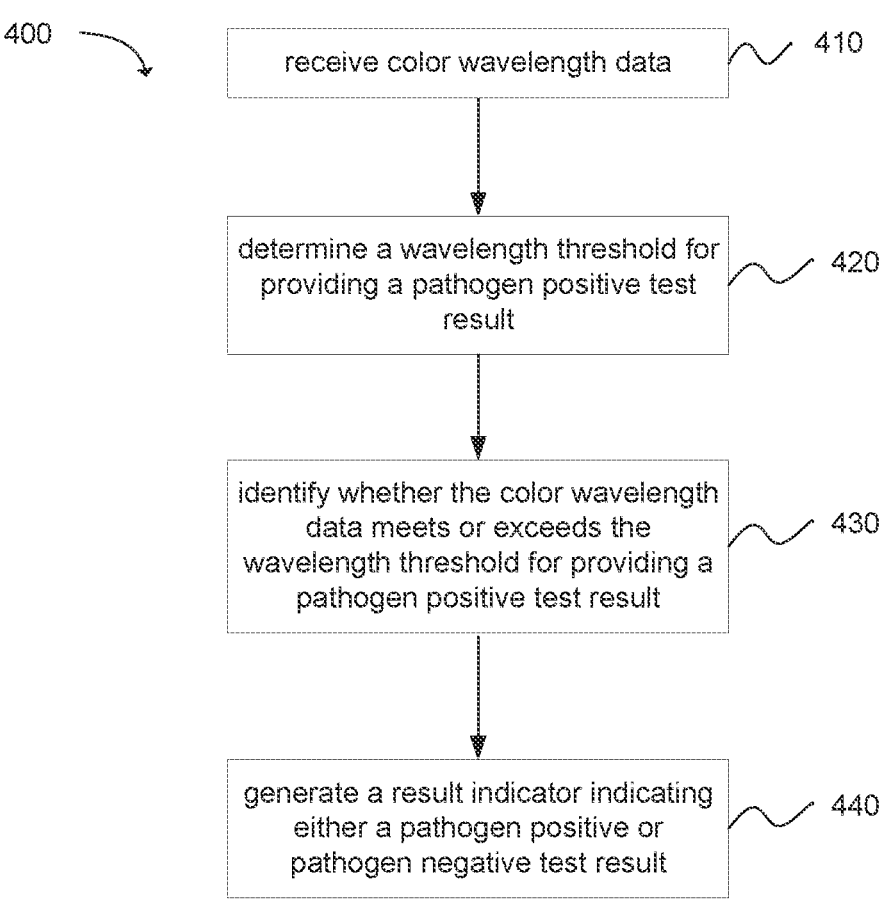
FIG. 4 depicts a system for identifying a colorimetric test result from a pathogen test performed on a solid phase substrate in accordance with an example embodiment.

Another example provides functionality 400 of a system for identifying a colorimetric test result from a pathogen test performed on a solid phase substrate, as shown in the flow chart in FIG. 4. The system can comprise a sensor configured to detect a spectrum of color wavelengths. The system can further comprise one or more processors. The one or more processors can be configured to receive color wavelength data, as shown in block 410. The one or more processors can be configured to determine a wavelength threshold for providing a pathogen positive test result, as shown in block 420. The one or more processors can be configured to identify whether the color wavelength data meets or exceeds the wavelength threshold for providing a pathogen positive test result, as shown in block 430. The one or more processors can be configured to generate a result indicator indicating either a pathogen positive or pathogen negative test result, as shown in block 440.

Another example provides a method 500 of identifying a test result of a loop-mediated isothermal amplification (LAMP) reaction on a solid phase reaction medium, as shown in the flow chart in FIG. 5. The method can comprise detecting, using a sensor component, a spectrum of color wavelengths, as shown in block 510. The method can comprise receiving, at one or more processors, color wavelength data from the sensor component, as shown in block 520. The method can comprise determining, at the one or more processors, whether the color wavelength data meets or exceeds the wavelength threshold for providing a positive test result, as shown in block 530. The method can comprise generating, at the one or more processors, a result indicator indicating either a positive or negative test result, as shown in block 540. The method can comprise displaying, at a user interface, a test result based on the result indicator, as shown in block 550.

Figure 6:
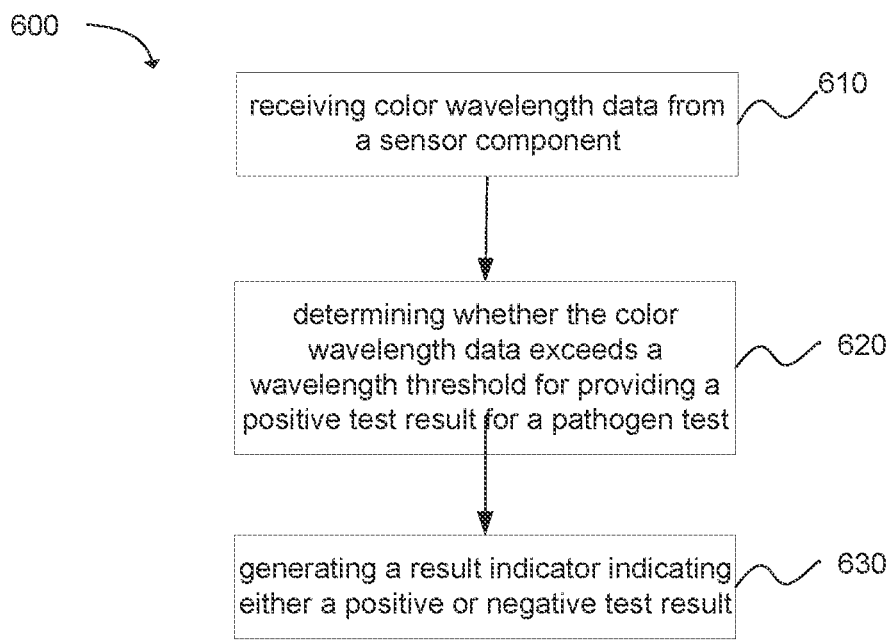
FIG. 6 depicts a flowchart of a machine readable storage medium having instructions embodied thereon for identifying a test result of a loop-mediated isothermal amplification (LAMP) reaction in accordance with an example embodiment.

Another example provides at least one machine readable storage medium having instructions 600 embodied thereon for identifying a test result of a loop-mediated isothermal amplification (LAMP) reaction, as shown in FIG. 6. The instructions can be executed on a machine, where the instructions are included on at least one computer readable medium or one non-transitory machine readable storage medium. The instructions when executed can perform: receiving, at the one or more processors, color wavelength data from a sensor component, as shown in block 610. The instructions when executed can perform: determining, at the one or more processors, whether the color wavelength data exceeds a wavelength threshold for providing a positive test result, as shown in block 620. The instructions when executed can perform: generating, at the one or more processors, a result indicator indicating either a positive or negative test result, as shown in block 630.

Figure 7:
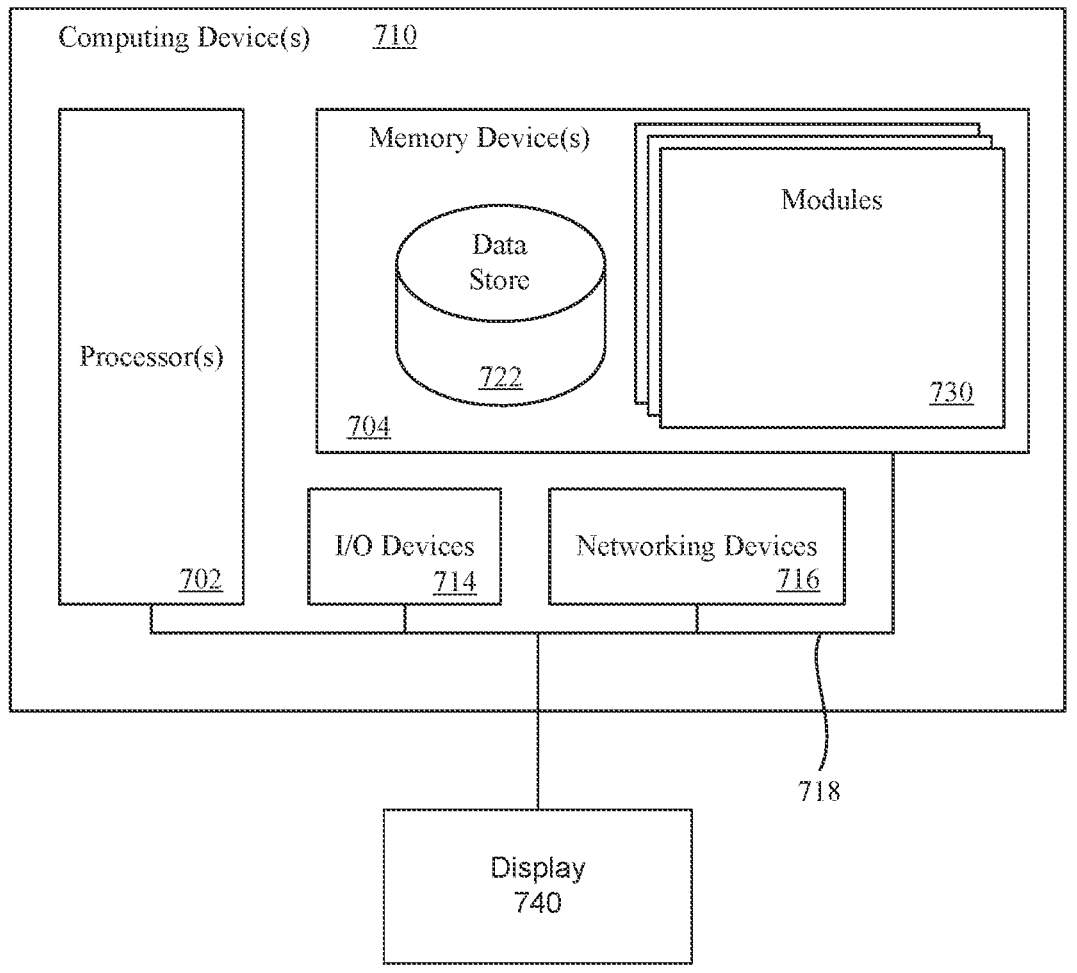
FIG. 7 illustrates a computing system that includes a data storage device in accordance with an example embodiment.

FIG. 7 illustrates a general computing system or device 700 that can be employed in the present technology. The computing system 700 can include a processor 702 in communication with a memory 704. The memory 704 can include any device, combination of devices, circuitry, and the like that is capable of storing, accessing, organizing, and/or retrieving data. Non-limiting examples include SANs (Storage Area Network), cloud storage networks, volatile or non-volatile RAM, phase change memory, optical media, hard-drive type media, and the like, including combinations thereof.

The computing system or device 700 additionally includes a local communication interface 718 for connectivity between the various components of the system. For example, the local communication interface can be a local data bus and/or any related address or control busses as may be desired.

The computing system or device 700 can also include an I/O (input/output) interface 714 for controlling the I/O functions of the system, as well as for I/O connectivity to devices outside of the computing system 700. A network interface 716 can also be included for network connectivity. The network interface 716 can control network communications both within the system and outside of the system. The network interface can include a wired interface, a wireless interface, a Bluetooth interface, optical interface, and the like, including appropriate combinations thereof. Furthermore, the computing system 700 can additionally include a user interface 714, a display device 740, as well as various other components that would be beneficial for such a system.

The processor 702 can be a single or multiple processors, and the memory 704 can be a single or multiple memories. The local communication interface 718 can be used as a pathway to facilitate communication between any of a single processor, multiple processors, a single memory, multiple memories, the various interfaces, and the like, in any useful combination.

EXAMPLES

In one example there is provided, a system for identifying a colorimetric test result from a pathogen test performed on a solid phase substrate that can comprise a sensor configured to detect a spectrum of color wavelengths; and one or more processors configured to: receive color wavelength data; determine a wavelength threshold for providing a pathogen positive test result; identify whether the color wavelength data meets or exceeds the wavelength threshold for providing a pathogen positive test result; and generate a result indicator indicating either a pathogen positive or pathogen negative test result.

In one example of a system for identifying a colorimetric test result from a pathogen test performed on a solid phase substrate, the one or more processors can be further configured to: adjust the wavelength threshold based on a material group identifier.

In another example of a system for identifying a colorimetric test result from a pathogen test performed on a solid phase substrate, the material group identifier can be based on one or more of: an average color wavelength of a material group, a median color wavelength of the material group, a variance of the color wavelength of the material group, a manufacturing date and time of the material group, one or more reagent types of the material group, or one or more solid-phase reaction medium types of the material group.

In another example of a system for identifying a colorimetric test result from a pathogen test performed on a solid phase substrate, the one or more processors can be further configured to: generate the material group identifier from color wavelength data aggregated from crowd-sourced data.

In another example of a system for identifying a colorimetric test result from a pathogen test performed on a solid phase substrate, the one or more processors can be further configured to: calculate a number of nucleic acid copies based on one or more of the color wavelength data, the material group identifier, or a color change time.

In another example of a system for identifying a colorimetric test result from a pathogen test performed on a solid phase substrate, the one or more processors can be further configured to: generate a confidence level using the color wavelength data and the material group identifier.

In another example of a system for identifying a colorimetric test result from a pathogen test performed on a solid phase substrate, the one or more processors can be further configured to: receive the color wavelength data for discrete sections of the pathogen test; determine the wavelength threshold for providing a pathogen positive test result based on the color wavelength data for discrete sections of the pathogen test; and identify whether the color wavelength data meets or exceeds the threshold for providing the pathogen positive test result.

In another example of a system for identifying a colorimetric test result from a pathogen test performed on a solid phase substrate, the one or more processors can be further configured to generate a confidence level for the pathogen positive test result based on the color wavelength data received from the discrete sections of the pathogen test.

In another example of a system for identifying a colorimetric test result from a pathogen test performed on a solid phase substrate, the one or more processors can be further configured to: receive the color wavelength data for discrete sections of the pathogen test; determine an additional wavelength threshold for providing a different pathogen positive test result based on the color wavelength data for discrete sections of the pathogen test; and generate an additional result indicator indicating either an additional pathogen positive or additional pathogen negative test result when the discrete sections of the pathogen test are targeted to different pathogens.

In another example of a system for identifying a colorimetric test result from a pathogen test performed on a solid phase substrate, the sensor can be configured to detect a spectrum of color wavelengths for discrete sections of the pathogen test.

In another example of a system for identifying a colorimetric test result from a pathogen test performed on a solid phase substrate, the sensor can comprise an RGB sensor configured to generate RGB values or a CMYK sensor configured to generate CMYK values.

In another example of a system for identifying a colorimetric test result from a pathogen test performed on a solid phase substrate, the sensor can comprise: a white light emitter; and a light receiver having a 540 nm filter.

In another example of a system for identifying a colorimetric test result from a pathogen test performed on a solid phase substrate, the one or more processors can be further configured to: adjust the wavelength threshold using color wavelength data having a wavelength from about 500 nm to about 565 nm.

In another example of a system for identifying a colorimetric test result from a pathogen test performed on a solid phase substrate, the sensor can be one or more of: a photoconductive sensor, a photovoltaic sensor, a photodiode sensor, a phototransistor sensor, or combinations thereof.

In another example of a system for identifying a colorimetric test result from a pathogen test performed on a solid phase substrate, the system can further comprise a graphical user interface configured to display the pathogen negative or pathogen positive test result.

In another example there is provided, a method of identifying a test result of a loop-mediated isothermal amplification (LAMP) reaction on a solid phase reaction medium that can comprise: detecting, using a sensor component, a spectrum of color wavelengths; receiving, at one or more processors, color wavelength data from the sensor component; determining, at the one or more processors, whether the color wavelength data meets or exceeds the wavelength threshold for providing a positive test result; generating, at the one or more processors, a result indicator indicating either a positive or negative test result; and displaying, at a user interface, a test result based on the result indicator.

In another example of a method of identifying a test result of a loop-mediated isothermal amplification (LAMP) reaction on a solid phase reaction medium, the method can further comprise adjusting, at the one or more processors, the wavelength threshold using RGB values or CMYK values from a material group identifier.

In another example of a method of identifying a test result of a loop-mediated isothermal amplification (LAMP) reaction on a solid phase reaction medium, the method can further comprise receiving, at the one or more processors, RGB values or CMYK values from the spectrum of color wavelengths.

In another example of a method of identifying a test result of a loop-mediated isothermal amplification (LAMP) reaction on a solid phase reaction medium, the method can further comprise generating, at the one or more processors, the result indicator indicating either the positive or negative test result based on the RGB or CMYK values.

In another example of a method of identifying a test result of a loop-mediated isothermal amplification (LAMP) reaction on a solid phase reaction medium, at least one machine readable storage medium having instructions embodied thereon for identifying a test result of a loop-mediated isothermal amplification (LAMP) reaction, the instructions when executed by one or more processors can perform the following: receiving color wavelength data from a sensor component; determining whether the color wavelength data exceeds a wavelength threshold for providing a positive test result for a pathogen test; and generating a result indicator indicating either a positive or negative test result.

In another example of a method of identifying a test result of a loop-mediated isothermal amplification (LAMP) reaction on a solid phase reaction medium, the method can further comprise instructions that when executed perform: adjusting the wavelength threshold based on a material group identifier.

In another example of a method of identifying a test result of a loop-mediated isothermal amplification (LAMP) reaction on a solid phase reaction medium, the material group identifier is based on one or more of: an average color wavelength of a material group, a median color wavelength of the material group, a variance of the color wavelength of the material group, a manufacturing date and time of the material group, one or more reagent types of the material group, or one or more solid-phase reaction medium types of the material group.

In another example of a method of identifying a test result of a loop-mediated isothermal amplification (LAMP) reaction on a solid phase reaction medium, further comprising instructions that when executed perform: generating the material group identifier from color wavelength data aggregated from crowd-sourced data.

In another example of a method of identifying a test result of a loop-mediated isothermal amplification (LAMP) reaction on a solid phase reaction medium, the method can further comprise instructions that when executed perform: calculating a number of nucleic acid copies based on the color wavelength data and the material group identifier.

In another example of a method of identifying a test result of a loop-mediated isothermal amplification (LAMP) reaction on a solid phase reaction medium, the method can further comprise instructions that when executed perform: generating a confidence level using the color wavelength data and the material group identifier.

In another example of a method of identifying a test result of a loop-mediated isothermal amplification (LAMP) reaction on a solid phase reaction medium, the method can further comprise instructions that when executed perform: generating a result indicator indicating either a positive or negative test result for a plurality of pathogens based on color wavelength data received for discrete sections of the pathogen test.

Various techniques, or certain aspects or portions thereof, can take the form of program code (i.e., instructions) embodied in tangible media, such as floppy diskettes, compact disc-read-only memory (CD-ROMs), hard drives, non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a random-access memory (RAM), erasable programmable read only memory (EPROM), flash drive, optical drive, magnetic hard drive, solid state drive, or other medium for storing electronic data. The low energy fixed location node, wireless device, and location server can also include a transceiver module (i.e., transceiver), a counter module (i.e., counter), a processing module (i.e., processor), and/or a clock module (i.e., clock) or timer module (i.e., timer). One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

As used herein, the term processor can include general purpose processors, specialized processors such as VLSI, FPGAs, or other types of specialized processors, as well as base band processors used in transceivers to send, receive, and process wireless communications.

It should be understood that many of the functional units described in this specification have been labeled as modules, in order to more particularly emphasize their implementation independence. For example, a module can be implemented as a hardware circuit comprising custom very-large-scale integration (VLSI) circuits or gate arrays, off-the-shelf semiconductors such as logic chips, transistors, or other discrete components. A module can also be implemented in programmable hardware devices such as field programmable gate arrays, programmable array logic, programmable logic devices or the like.

In one example, multiple hardware circuits or multiple processors can be used to implement the functional units described in this specification. For example, a first hardware circuit or a first processor can be used to perform processing operations and a second hardware circuit or a second processor (e.g., a transceiver or a baseband processor) can be used to communicate with other entities. The first hardware circuit and the second hardware circuit can be incorporated into a single hardware circuit, or alternatively, the first hardware circuit and the second hardware circuit can be separate hardware circuits.

Modules can also be implemented in software for execution by various types of processors. An identified module of executable code can, for instance, comprise one or more physical or logical blocks of computer instructions, which can, for instance, be organized as an object, procedure, or function. Nevertheless, the executables of an identified module need not be physically located together, but can comprise disparate instructions stored in different locations which, when joined logically together, comprise the module and achieve the stated purpose for the module.

Indeed, a module of executable code can be a single instruction, or many instructions, and can even be distributed over several different code segments, among different programs, and across several memory devices. Similarly, operational data can be identified and illustrated herein within modules, and can be embodied in any suitable form and organized within any suitable type of data structure. The operational data can be collected as a single data set, or can be distributed over different locations including over different storage devices, and can exist, at least partially, merely as electronic signals on a system or network. The modules can be passive or active, including agents operable to perform desired functions.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A system for identifying a colorimetric test result from a pathogen test performed on a solid phase substrate comprising:

a sensor configured to detect a spectrum of color wavelengths; and one or more processors configured to:

receive color wavelength data;

determine a wavelength threshold for providing a pathogen positive test result;

identify whether the color wavelength data meets or exceeds the wavelength threshold for providing a pathogen positive test result; and generate a result indicator indicating either a pathogen positive or pathogen negative test result;

wherein the one or more processors are further configured to:

receive the color wavelength data for discrete sections of the pathogen test;

determine an additional wavelength threshold for providing a different pathogen positive test result based on the color wavelength data for discrete sections of the pathogen test; and generate an additional result indicator indicating either an additional pathogen positive or additional pathogen negative test result when the discrete sections of the pathogen test are targeted to different pathogens.

2. The system of claim 1, wherein the one or more processors are further configured to:

adjust the wavelength threshold based on a material group identifier.

3. The system of claim 2, wherein the material group identifier is based on one or more of:

an average color wavelength of a material group, a median color wavelength of the material group, a variance of the color wavelength of the material group, a manufacturing date and time of the material group, one or more reagent types of the material group, or one or more solid-phase reaction medium types of the material group.

4. The system of claim 2, wherein the one or more processors are further configured to:

generate the material group identifier from color wavelength data aggregated from crowd-sourced data.

5. The system of claim 2, wherein the one or more processors are further configured to:

calculate a number of nucleic acid copies based on one or more of the color wavelength data, the material group identifier, or a color change time.

6. The system of claim 2, wherein the one or more processors are further configured to:

generate a confidence level using the color wavelength data and the material group identifier.

7. The system of claim 1, wherein the one or more processors are further configured to:

generate a confidence level for the pathogen positive test result based on the color wavelength data received from the discrete sections of the pathogen test.

8. The system of claim 1, wherein the sensor comprises an RGB sensor configured to generate RGB values or a CMYK sensor configured to generate CMYK values.

9. The system of claim 1, wherein the sensor comprises:

a white light emitter; and a light receiver having a 540 nm filter.

10. The system of claim 1, wherein the one or more processors are further configured to:

adjust the wavelength threshold using color wavelength data having a wavelength from about 500 nm to about 565 nm.

11. The system of claim 1, wherein the sensor is one or more of: a photoconductive sensor, a photovoltaic sensor, a photodiode sensor, a phototransistor sensor, or combinations thereof.

12. The system of claim 1, further comprising a graphical user interface configured to display the pathogen negative or pathogen positive test result.

13. A method of identifying a test result of a loop-mediated isothermal amplification (LAMP) reaction on a solid phase reaction medium, comprising:

detecting, using a sensor component, a spectrum of color wavelengths;

receiving, at one or more processors, color wavelength data from the sensor component;

determining, at the one or more processors, whether the color wavelength data meets or exceeds the wavelength threshold for providing a positive test result;

generating, at the one or more processors, a result indicator indicating either a positive or negative test result; and displaying, at a user interface, a test result based on the result indicator;

receiving, at the one or more processors, the color wavelength data for discrete sections of the solid phase reaction medium;

determining, at the one or more processors, an additional wavelength threshold for providing a different pathogen positive test result based on the color wavelength data for discrete sections of the solid phase reaction medium; and generating, at the one or more processors, an additional result indicator indicating either an additional pathogen positive or additional pathogen negative test result when the discrete sections of the solid phase substrate are targeted to different pathogens.

14. The method of claim 13, further comprising:

adjusting, at the one or more processors, the wavelength threshold using RGB values or CMYK values from a material group identifier.

15. The method of claim 13, further comprising:

receiving, at the one or more processors, RGB values or CMYK values from the spectrum of color wavelengths.

16. The method of claim 15, further comprising:

generating, at the one or more processors, the result indicator indicating either the positive or negative test result based on the RGB or CMYK values.

\* \* \* \* \*